United States Patent [19]

Kleiner et al.

[11] 4,075,237
[45] Feb. 21, 1978

[54] PERFLUORINATED ESTERS OF FUMARIC ACID AND CERTAIN OTHER ETHYLENICALLY UNSATURATED POLY-BASIC ACID AND SOIL REPELLANT POLYMERS THEREOF

[75] Inventors: Eduard K. Kleiner, Dobbs Ferry; Martin Knell, Ossining, both of N.Y.

[73] Assignee: Geigy Chemical Corporation, Ardsley, N.Y.

[21] Appl. No.: 720,370

[22] Filed: Apr. 10, 1968

[51] Int. Cl.$^2$ ............... C07C 67/16; C07C 69/60
[52] U.S. Cl. ............... 260/455 R; 260/79.5 R; 260/453 RY; 526/242
[58] Field of Search ............... 260/78.4 E, 78.5 B, 260/78.5 E, 485 F, 485 J, 455, 481 R, 79.5, 486 H, 453

[56] References Cited

U.S. PATENT DOCUMENTS

| | | | |
|---|---|---|---|
| 2,642,416 | 6/1953 | Albrecht et al. | 260/83.5 |
| 3,102,103 | 8/1963 | Albrecht et al. | 260/29.6 |
| 3,128,303 | 4/1964 | Zimmerman | 260/485 |
| 3,219,687 | 11/1965 | Zisman et al. | 260/485 |
| 3,385,882 | 5/1968 | Tullio | 260/485 |
| 3,594,353 | 7/1971 | Domba | 260/78.4 |

*Primary Examiner*—John Kight, III
*Attorney, Agent, or Firm*—Edward McC. Roberts; Prabodh I. Almaula

[57] ABSTRACT

Monomeric esters of fumaric, maleic, citraconic, mesaconic, itaconic, aconitic, or methylene malonic acid and alcohols of the formula $C_mF2_{m+1}C_nH2_nOH$ and mercaptans of the formula $C_mF2_{m+1}C_nH2_nSH$ form homopolymers and form copolymers with other ethylenically unsaturated comonomers. The polymers obtained have valuable soil repellent properties and are especially useful in textile finishes. Preferred compounds are bis (1,1,2,2-tetrahydroperfluorononyl) fumarate and bis (1,1-dihydroperfluorooctyl) fumarate.

2 Claims, No Drawings

PERFLUORINATED ESTERS OF FUMARIC ACID AND CERTAIN OTHER ETHYLENICALLY UNSATURATED POLY-BASIC ACID AND SOIL REPELLANT POLYMERS THEREOF

THE INVENTION

The invention relates to novel monomers and the polymers which may be prepared from them. The resulting polymers possess excellent soil repellent properties. These polymers provide oil and water repellent finishes useful to treat materials such as textiles, paper, leather, painted wooden and metallic surfaces and the like.

The monomer compounds of the present invention are of the following formula:

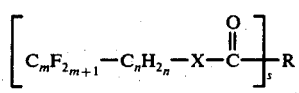

FORMULA I wherein $m$ is an integer of 3 to 18, preferably 6 to 12, and most preferably 7 to 10;

$n$ is an integer of 0 to 10, preferably 1 or 2;

X is oxygen or sulfur, preferably oxygen;

R is an ethylenically unsaturated hydrocarbon radical derived from fumaric, maleic, citraconic, mesaconic, itaconic, aconitic, or methylene malonic acid, preferably fumaric; and $s$ is an integer of 2 or 3 and is equal to the number of carboxyl groups of the acid from which R is derived, preferably being 2 to correspond to fumaric acid.

The corresponding polymers of this invention are thus those having a skeletal chain comprising repeating units of

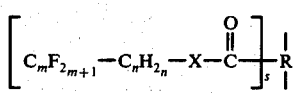

FORMULA II wherein $m$, $n$, X, R and $s$ have the same meaning as given in FORMULA I.

The polymers of the present invention are particularly valuable in fabric finishes. Finishes made with the polymers of the present invention are fast to repeated washes and drycleanings. Thus fabrics treated with such finishes maintain their soil repellency for long durations.

Particularly preferred embodiments of the present invention are polymers of the compounds bis (1,1-dihydroperfluorooctyl) fumarate and bis (1,1,2,2-tetrahydroperfluorononyl) fumarate.

It should be noted that the lower unit for the value of $m$ is particularly important. Polymers of corresponding compounds in which $m$ is lower than 3 are not suitable for use in soil repellent finishes. For example, polymers of bis (trifluoroethyl) fumarate have no practical utility in soil repellent finishes.

Since the novel fluoropolymers and copolymers find substantial use as textile finishes, it is an advantage to include in the monomer mixture from about 0.2 to about 5% by weight of a reactive acrylic, which permits crosslinking either by heat or crosslinking agents. Such reactive fluorocopolymers give textile finishes with superior resistance to washing, dry cleaning, scrubbing, abrasion and crushing, both wet and dry, and also a better durability of the oil and water repellency.

The polymers contemplated by the present invention thus include homopolymers, copolymers with other ethylenically unsaturated monomers, and physical blends of such homopolymers and copolymers together and/or with other polymers.

It is also uniquely advantageous, especially in the preparation of fabric finishes, to use blends of emulsions of the instant fluorinated polymers with emulsions of other polymers such as polyalkyl acrylates and polyalkyl methacrylates, illustrative of which is poly n-octyl methacrylate.

The monomer compounds of the present invention may be prepared following procedures familiar to those skilled in the art.

Starting materials employed are generally commercially available and/or may be prepared readily according to methods familiar to those skilled in the art.

It is to be understood that the perfluoroalkyl group may, if desired, be a mixture of varying chain length since basic starting materials are often obtained by telomerization procedures yielding $C_mF_{2m+1}I$ groups of varying length.

U.S. Pat. No. 3,226,449 is illustrative of one method useful for the preparation of certain perfluoroalkyl iodides which may be employed as starting materials in making the novel monomers of the present invention.

The ester monomers of this invention can generally be prepared by well known esterification reactions between: acids and perfluorinated alcohols, alkyl esters and perfluorinated alcohols, acid chloride and perfluorinated alcohols, acid salts and perfluorinated halogenids, and acid chlorides and perfluorinated alkoxides. Of course, it is understood that the corresponding mercaptans may be used in lieu of the alcohols.

Generally the reaction of acid chlorides with the perfluorinated alcohol or mercaptan is preferred since the acid chlorides are easily available and the esterification proceeds readily. An exception, of course, is the case of maleyl chloride and chloromaleyl chloride which do not exist.

The esterifications are carried out in the absence of a base.

The esters of methylene malonic acid generally require a two step synthesis. The intermediate malonesters are made using one of the above esterification techniques and then the methylene malonic ester is formed for example by condensation of the malonester with formaldehyde. See E. Haworth and W.H. Perkin, J. Chem. Soc. 73, 339 – 345 (1898).

Representative preparations of examples of alcohols and mercaptans useful as starting materials in the practice of this invention are disclosed in: U.S. Pat. Nos. 2,666,797; 3,283,012; 3,171,861; 3,285,975; 2,884,991; and French Pat. No. 1,221,415.

Other alcohols which may form esters with the above acids or derivatives thereof are those such as HO—$(CH_2)_n$CH=CH—$R_f$, disclosed in U.S. Pat. No. 3,285,975; HO—$CH_2CF_2CF_2$—O—$R_f$ disclosed in U.S. Pat. No. 2,826,564; and HO—$(CH_2)_nO(CH_2)_nR_f$ and HO$(CH_2)_nS(CH_2)_nR_f$ which are obtained by reduction of the corresponding $CH_3OCO(CH_2)_{n-6}O(CH_2)_mR_f$ esters described in U.S. Pat. No. 3,172,910.

It is believed that possibly the greater soil repellency properties obtained with finishes comprising polymers of the present invention in contrast to polymers derived from methacrylate and other monoesters such as disclosed for example in U.S. Pat. Nos. 3,282,905 and 3,239,557, is due to the closer packing of the perfluorinated groups in the present polymers.

Polymerization may be carried out in bulk, solution, suspensions, or emulsions. Solution and emulsion polymerization procedures are preferred. Preferred solvents for polymerization are hexafluoroxylene, benzotrifluoride, fluorohalogenated hydrocarbons, other fluorinated solvents, and the like.

As indicated above, the novel monomers of this invention may be homopolymerized or copolymerized with other ethylenically unsaturated comonomers. The preferred polymerization techniques are emulsion polymerization in an aqueous medium and solution polymerization.

In emulsion polymerization, the monomer or monomers to be polymerized are emulsified together in a water solution of a surface active agent to a given monomer concentration of from about 5 to about 50%. Usually the temperature is raised to between 40° and 70° C to effect polymerization in the presence of an added catalyst. A suitable catalyst may be any one of the commonly known agents for initiating the polymerization of an ethylenically unsaturated compound. The concentration of the catalyst for the polymerization is usually between 0.1 and 2% based upon the weight of the monomers.

Suitable surfactants or emulsifying agents include cationic, anionic or non-ionic types. Since the cationic types can be used in most textile treating baths, they are preferred. The hydrophobic portion of the surfactant may be hydrocarbon or fluorinated hydrocarbon.

Suitable surfactants that may be used include, for example, non-ionic surfactants in which the hydrophilic group is a poly(ethoxy) group and the hydrophobic portion is either a hydrocarbon or a fluorocarbon group such as the ethylene oxide condensates of alkyl phenols, alkanols, alkylamines, alkyl thiols, alkylcarboxylic acids, fluoroalkyl carboxylic acids, fluoroalkyl amides and the like.

Suitable cationic surfactants include for example quaternary ammonium salts or amine salts containing at least one long chain alkyl, fluoroalkyl, or high alkyl substituted benzene or naphthalene group to provide the hydrophobic portion.

Polymerization is preferably carried out for a reaction period adjusted to obtain essentially quantitative conversion of the fluorinated monomer. The optimum reaction time will depend upon the catalyst used and the polymerization temperature and other conditions, but will generally be in the range of from 0.5 to 24 hours.

The polymerization temperature will depend upon the catalyst chosen. In the case of emulsion polymerization in aqueous media, it will generally be in the range of from 20° to 90° C. The polymerization is generally most conveniently and preferably carried out at atmospheric pressure wherever possible.

In solution polymerization, the monomer or monomers are dissolved in a suitable solvent such as fluorinated solvents, for example, hexafluoroxylene, trifluorotoluene or mixtures thereof with acetone and/or ethylacetate and polymerized in a reaction vessel using initiators such as azobisisobutyronitrile or other azo initiators at concentrations of 0.1 to 2.0% at 40° – 100° C under nitrogen.

As mentioned, besides homopolymers, valuable copolymers are obtained by polymerization of the foregoing novel perfluorinated monomers with other polymerizable monomers having ethylene unsaturation.

As a general rule, the preferred comonomer units should have short side chains, since the comonomers with longer side chains generally tend to decrease the soil repellency level.

Typical of such monomers are vinyl ethers, α-olefins, vinyl esters, styrenes and related monomers.

Examples of suitable comonomers are alkyl vinylethers, such as methyl vinyl ether, isopropyl vinyl ether, isobutyl vinyl ether, vinyl 2-methoxy ethyl ether, n-propyl vinyl ether, t-butyl vinyl ether, isoamyl vinyl ether, n-hexyl vinyl ether, 2-ethylbutyl vinyl ether, diisopropylmethyl vinyl ether, 1-methyl-heptyl vinyl ether, n-decyl vinyl ether, n-tetradecyl vinyl ether, and n-octadecyl vinyl ether.

Also, vinyl ethers of the followng amino alcohols: ethanolamine vinyl ether, 2-dimethylamino ethanol vinyl ether, N-hydroxyethyl-m-toluidine vinyl ether, hydroxyethyl butyl aniline vinyl ether, and β-piperidinoethanol vinyl ether, and the like.

Also useful are gamma substituted ethers, such as α-methylvinyl methyl ether, α-methylvinyl ethyl ether, α-amylvinyl methyl ether, and α-phenylvinyl ethyl ether; alicyclic and aralkyl vinyl ethers such as cyclohexanol vinyl ether, menthol vinyl ether, carvacrol vinyl ether, benzyl alcohol vinyl ether, β-phenylethanol vinyl ether, tetrahydronaphthol vinyl ether, β-decahydronaphthol vinyl ether, methylphenyl carbinol vinyl ether, butyl-cyclohexanol vinyl ether, and dihydroabictinol vinyl ether.

Additionally, vinyl aryl ethers such as vinyl phenyl ether, α-bromovinyl phenyl ether, α-phenylvinyl phenyl ether, vinyl m-cresyl ether, α-methyl vinyl p-cresyl ether, vinyl p-chlorophenyl ether, vinyl 2,4,6-trichlorophenyl ether, and vinyl α-naphthyl ether.

Vinyl comonomers with short side chains are preferred.

Of All these vinyl ethers, the most preferred ones are: methyl vinyl ether, ethyl vinyl ether, n-propylvinyl ether, isopropyl vinyl ether, 2-methoxyethyl vinyl ether and 2-chloroethyl vinyl ether.

Propylene, butylene and isobutylene are preferred α-olefins useful as comonomers with the novel fluoro monomers of the present invention. Straight and branched chain α-olefins are useful with up to 18 carbon atoms in the side chain.

Useful copolymers of the novel perfluorinated compounds of the invention are formed with vinyl esters, e.g. vinyl acetate, vinyl esters of substituted acids, such as for example, vinyl methoxyacetate, vinyl trimethylacetate, vinyl isobutyrate, isopropenyl butyrate, vinyl lactate, vinylcaprylate, vinyl pelargonate, vinyl myristate, vinyl oleate and vinyl linoleate; vinyl esters of aromatic acids, such as vinyl benzoate, vinyl alkoxybenzoates, vinyloctylphthalate, vinyl tetrachlorobenzoate, vinyl β-phenyl butyrate, vinyl β-naphthoate, and vinyl ethyl phthalate; vinylformate and vinylcarbonate derivatives such as vinylformate, vinylchloroformate, methylvinylchloroformate, vinyl methyl carbonate, vinylethylcarbonate, vinylphenylcarbonate and vinylidenecarbonate; vinyl thioesters such as vinyl methyl sulfide, vinyl n-butyl sulfides, 1-chloroethyl vinyl sulfide, 2-chloroethyl vinyl sulfide, vinyl dodecyl sulfide, vinyl phenyl sulfide, vinyl o-cresyl sulfide, vinyl 2,5-dimethyl-4-chlorophenyl sulfide, vinyl 8-chloronaphthyl sulphide, and vinyl 2-benzothiazylsulfide.

Preferred of the foregoing vinyl esters are vinylacetate, vinyl propionate, vinylbenzoate, and isopropenylacetate.

Also useful as comonomers are styrene and related monomers which copolymerize readily with the novel esters of this invention such as o-methylstyrene, p-methylstyrene, 3,4-dimethyl styrene, 2,4,6-trimethyl styrene, m-ethyl styrene, 2,5-diethyl styrene, p-butyl styrene, m-t-butyl styrene, p-benzyl styrene, o-methoxy styrene, p-methoxystyrene, 6-methoxy-3-methyl styrene, 2,6-dimethoxy styrene, and 2-methoxy-5-isopropyl styrene; derivatives of α-methyl styrene, such as: 4-chloro α-methyl styrene, 3,4-dimethyl α-methylstyrene, 3-bromo-2-methyl α-methylstyrene, and 2,5-dichloro-α-methylstyrene; chlorostyrene derivatives, such as m-chlorostyrene, 2,3-dichlorostyrene, 3,4-dichlorostyrene, trichlorostyrene, and pentachlorostyrene; bromo- and fluorostyrene derivatives, such as p-bromostyrene, m-fluorostyrene, m-trifluoromethyl styrene, 4-fluoro-3-trifluoromethyl styrene, and pentafluorostyrene; other styrene derivatives such as p-formylstyrene, methyl ester of p-vinyl benzoic acid, p-vinylbenzyl alcohol, 1,4-dimethyl-2-hydroxystyrene, 3,5-dibromo-4-hydroxystyrene, 2-nitro-4-isopropylstyrene, p-N,N-dimethyl amino styrene, N-(vinyl benzyl) pyrrolidine and sulfoamido styrene; vinyl derivatives of biphenyl, naphthalene and related aromatic compounds, such as 4-chloro-4'-vinyl biphenyl, o-isopropenyl biphenyl, p-vinyl diphenyl oxide, 4-chloro-1-vinyl naphthalene, 1-chloro-4-vinyl naphthalene and 1-vinyl acinaphthalene; vinylfuran, vinylbenzofuran and vinylpyridine, such as 2-vinyl dibenzofuran, 5-ethyl-2-vinyl-thiophene, 5-chloro-2-vinyl thiophene, 3,4,5-trichloro-2-vinyl thiophene and 2-vinyl dibenzothiophene.

Additional useful comonomers are ethylene and chloro-, fluoro- and cyano- derivatives of alkylene, such as ethylene, vinylchloride, vinylidene-chloride, vinylfluoride, vinylidene fluoride, acrylonitrile, methacrylonitrile, tetrafluoroethylene, trifluorochloroethylene, hexafluoropropylene; acrylate and methacrylate monomers, particularly those with 1 to 12 carbon atoms in the ester groups such as monofluoroethyl methacrylate, n-propyl methacrylate, 2-methyl cyclohexyl methacrylate, ethylene glycol mono-methacrylate, β-bromoethyl methacrylate, β-phenyl ether methacrylate, o-cresyl methacrylate, and β-naphthyl methacrylate, methyl methacrylate, t-butyl methacrylate, n-butyl methacrylate, methylacrylate, ethylacrylate, propylacrylate, butylacrylate, 3-methyl-1-pentylacrylate, octylacrylate, tetradecylacrylate, s-butylacrylate, 2-ethylhexyl acrylate, 2-methoxyethyl acrylate, and phenyl acrylate; α-halogen acrylates, such as methyl chloro acrylate, methyl bromo acrylate, ethyl chloro acrylate, s-butyl chloro acrylate, cyclohexyl chloro acrylate, phenyl chloro acrylate, cyclohexyl bromo acrylate, n-propyl chloro acrylate, isopropyl chloro acrylate, n-butyl-chloro acrylate, and methyl fluoro acrylate; dienes particularly 1,3-butadiene, isoprene, and chloroprene, 2-fluoro-butadiene, 1,1,3-trifluorobutadiene, 1,1,2,3-tetrafluoro butadiene, 1,1,2-trifluoro-3,4-dichlorobutadiene and tri- and pentafluoro butadiene and isoprene; nitrogen-vinyl monomers such as N-vinylimides, amides, and secondary cyclic amines, like vinyl succinimide, vinyl pyrrolidone, N-vinyl carbazole and the like.

Also useful as comonomers with some of the novel monomers of the present invention are vinyl monomers which contain perfluorinated side chains. Examples of such perfluorinated monomers are vinyl ethers of the type disclosed in U.S. Pat. Nos. 2,732,370 and 2,828,025; vinyl esters containing fluorinated alkyl groups disclosed in U.S. Pat. Nos. 2,592,069 and 2,436,144. Other useful monomers are acrylates and methacrylates and derivatives thereof such as those disclosed in U.S. Pat. Nos. 2,628,958; 3,256,230; 2,839,513; 3,282,905; 3,252,932 and 3,304,278.

As mentioned, it may also be desirable to include a minor amount of other reactive comonomers in order to improve the wash and dry-clean properties of the novel textile finishes obtained according to the practice of this invention. Such monomers act as cross-linking agents during the curing operation. Such reactive comonomers are generally employed in amounts of 0.1 to 2%.

During the preparation of the novel monomers of this invention, a small percentage of the half esters is formed as side products and serve as reactive comonomers.

Other reactive monomers which may be included are by way of illustration: acrylic acid, methacrylic acid, acrylamide, methacrylamide, N-methylolacrylamide, 2-hydroxyethylmethacrylate or -acrylate, hydroxypropylacrylates or methacrylates, and t-butylaminoethylmethacrylate glycidylmethylate. Of the foregoing, N-methylolacrylamide and 2-hydroxyethylmethacrylate are preferred.

Coatings of the homopolymers and copolymers according to the present invention can be prepared and applied from solvent solutions or from aqueous emulsions. Suitable solvents are fluoroalkanes, fluorochloroalkanes, fluoroalkylsubstituted aromatics, alkyl esters of perfluoroalkanoic acids, chlorinated alkanes or aromatics, hydrocarbon aromatics, ketones, esters and ethers. Especially useful as solvents are the fluorinated liquids, and especially α,α,α-trifluorotoluene, otherwise known as benzotrifluoride, hexafluoroxylene and mixtures of these with ethyl acetate or acetone and the like. Concentrations of the fluorinated polymers of the present invention in solvent to provde coatings with effective oil and water repellency properties will generally be of the order of 0.01 to 10% and preferably from 0.1 to 2.0% by weight. Blends of the emulsions of the polymers of this invention with blended emulsions of other polymers and copolymers are particularly useful in textile finishes. The polymers and copolymers are generally of a non-fluorinated type; however, as indicated below other fluorinated polymers and copolymers may be used if desired. Non-fluorinated polymers useful in such blends, include for example, but without limitation, polymers and copolymers of alkyl acrylates and alkyl methacrylates, such as methyl methacrylate, ethyl methacrylate, hexyl methacrylate, and n-octyl methacrylate. A particularly suitable polymer is poly-n-octyl methacrylate. Also useful are polymers and copolymers of acrylic acid, methacrylic acid, styrene, alkyl styrene, butadiene, 2-methyl-1,3-butadiene, 2-chloro-1,3-butadiene; polymers and copolymers of vinyl esters such as vinyl acetate, vinyl butyrate, vinyl laurate, vinyl stearate, vinyl 2-ethyl-hexanoate; polymers and copolymers of vinyl halides and vinylidene halides, such as vinyl chloride, vinylidene chloride, vinyl fluoride, vinylidene fluoride; polymers and copolymers of allyl esters such as allyl propionate, or allyl caprylate; polymers and copolymers of vinyl ketones, such as vinyl methyl ketone, vinyl ethyl ketone, and the like; polymers and copolymers of vinyl ethers such as methyl vinyl ether, cetyl vinyl ether, and the like; polymers and copolymers of acrylamide, methacrylamide, N-methylol acrylamide, N-methylol methacrylamide, N-isopropyl acrylamide, and acrylonitrile and methacrylonitrile.

For example, from about 20 to 97% by weight of a homopolymer of poly-n-octyl methacrylate blended with the polymers of this invention provides very useful coating compositions which retain surprisingly high repellency ratings even though the relative amount of perfluorinated polymer of this invention is relatively low. Of course, it is understood that besides application to textiles, the coatings of the perfluorinated polymers of the present invention are useful in providing oil and water repellent coatings for leather, paper, wood, masonry, metals, plastics, glass, painted surfaces, and the like. Coatings may be readily applied by various coating techniques, such as those familiar to the art, such as dipping, spraying, brushing, padding, roll coating, and the like.

For evaluation purposes, the textile material in the following examples was dipped in the bath comprising the polymer to be evaluated and the amount of the retained solution adjusted so as to leave approximately 2% of latex by weight of the fabric on the fabric. The fabric is dried at room temperature and then cured in an oven at a temperature of about 175° C for about 2 minutes.

The type of textile material which is coated is not at all critical. For evaluation purposes, repellency ratings for cotton or wool are determined as a standard screening procedure; however, such fibers such as fiberglass, silk, regenerated cellulose, cellulose esters and ethers, polyamides, polyesters, polyacrylonitrile, polyacrylic esters and other fibers alone or blended or in combination may be coated with the polymers of the present invention.

In the present examples below, the repellency ratings were determined as follows:

The AATCC water spray test rating was determined according to Standard Test method 22-1966 of the American Association of Textile Chemists and Colorists, XXXVII, 1961, p. 1952 (also designated ASTM-D 583-58).

Oil repellency is measured by the 3-M-Oil test procedure of Grajek and Peterson, Textile Research Journal, April 1962, p. 323.

The cotton/polyester fabric referred to in the evaluation is a 65% polyester-35% cotton blend. The polyester is one formed from ethylene glycol and terephthalic acid, sold for example under the Dacron trademark.

The following examples describing certain representative embodiments of this invention will serve to further illustrate the nature of this invention. It is to be understood that the examples are merely illustrative and intended to enable those skilled in the art to practice the invention in all of the embodiments flowing therefrom and do not in anyway limit the scope of the invention defined in the claims. Unless otherwise specified, the relationship of parts by weight to parts by volume is that of grams to cubic centimeters, and temperatures are ° C.

EXAMPLE 1 a. Bis (1,1-Dihydroperfluorobutyl) Fumarate

A mixture of 15.3 parts of fumaryl chloride and 40 parts of 1,1-dihydroperfluorobutyl alcohol is heated with stirring at 90° – 5° until no further hydrogen chloride is liberated. After a total reaction time of 120 hours, the product is isolated by distillation. In this manner, 18.0 parts of bis (1,1-dihydroperfluorobutyl) fumarate boiling at 106° – 11° at 5 mm pressure and melting at 45° – 45.5° is obtained.

Analysis for $C_{12}H_6F_{14}O_4$: Calculated: C, 30.01; H, 1.25. Found: C, 29.97; H, 1.28.

b. Mixed Bis (1,1,2,2-Tetrahydroperfluoroalkyl) Fumarate

The procedure of (a) is repeated, using 120 parts of a mixture containing 42.0% $C_6F_{13}CH_2CH_2OH$, 35.8% $C_8F_{17}CH_2CH_2OH$, 21.0% $C_{10}F_{21}CH_2CH_2OH$, 1.0% $C_{12}F_{25}CH_2CH_2OH$ and 0.2% $C_{14}F_{29}CH_2CH_2OH$ instead of the 1,1-dihydroperfluorobutyl alcohol. After 5 hours of heating at 95° – 100°, VPC indicated that the reaction is essentially complete. Distillation of the product gives 93 parts of mixed fumarate diesters boiling at 145° – 207° at 0.020 mm. pressure and having the following microanalysis: C, 28.69; H, 1.05; F, 63.54.

EXAMPLE 2

Bis (1,1-Dihydroperfluorooctyl) Fumarate

A mixture of 57.5 parts of fumaryl chloride and 300 parts of 1,1-dihydroperfluorooctyl alcohol is heated with stirring at 80° – 5° until no further hydrogen chloride is liberated. The total reaction time is 141 hours. After two recrystallizations from isopropyl alcohol, 196.2 parts of bis (1,1-dihydroperfluorooctyl) fumarate, melting at 74° – 7° obtained. Further purification yields material melting at 80° – 82.5° which is identified by microanalysis, IR and NMR spectroscopy.

EXAMPLE 3

Bis (1,1,2,2-Tetrahydroperfluorooctyl) Fumarate

A mixture of 9.46 parts of 1,1,2,2-tetrahydroperfluorooctanol (prepared as described in U.S. Pat. No. 3,283,012), 1.87 parts of dimethyl fumarate, 0.55 parts of concentrated sulfuric acid, and 100 parts by volume of toluene is placed in a pear shaped flask fitted with a short Vigreux distilling column. Toluene is distilled until no further methanol is detected in the distillate. Additional toluene is added as needed to the reaction flask during the reaction. On cooling, the product crystallizes from the toluene, and is filtered, and washed with water until the washings are neutral. After two recrystallizations from toluene and one from hexane, 1.4 parts of bis (1,1,2,2-tetrahydroperfluorooctyl) fumarate melting at 56° – 72° is obtained. Although the compound does not melt sharp, VPC, IR, NMR and microanalysis indicate that it is pure and has the desired structure.

Analysis for $C_{20}H_{10}F_{26}O_4$: Calculated: C, 29.72; H, 1.25; F, 61.12. Found: C, 29.53; H, 1.40; F, 60.76.

EXAMPLE 4

Bis (1,1,2,2-Tetrahydroperfluorononyl) Fumarate

A solution of 2.68 parts of fumaryl chloride and 14.5 parts of 1,1,2,2-tetrahydroperfluorononyl alcohol (prepared as described in U.S. Pat. No. 3,283,012) in 45.0 parts by volume of acetonitrile is allowed to stand overnight at room temperature. The reaction mixture is then heated with stirring at 80° for 3 hours. After cooling in an ice bath, the product is separated by filtration, washed with cold acetonitrile and air dried. 8.9 Parts of crude product are obtained. After two recrystallizations from isopropyl alcohol the melting point is 81° – 83.5° and the IR, NMR and microanalysis conform with the expected structure.

Analysis for $C_{22}H_{10}F_{30}O_4$: Calculated: C, 29.09; H, 1.11; F, 62.75. Found: C, 28.91; H, 1.24; F, 62.94.

EXAMPLE 5

Bis (Hexafluoroisopropyl) Fumarate

To a slurry of 2.4 parts of sodium hydride, as a 50% dispersion in mineral oil, in 45 parts of toluene, cooled to 15°, is added with stirring 25.2 parts of hexafluoroisopropyl alcohol keeping the temperature below 30°. A solution of 7.7 parts of fumaryl chloride in 10 parts of toluene is then added dropwise with stirring keeping the temperature below 30°. The reaction mixture is stirred for 1½ hours at room temperature and heated to boiling. After cooling to room temperature, 100 parts of water is added. The toluene layer is separated, washed two times with 50 parts of water, dried over anhydrous magnesium sulfate, and distilled through an 18 inch spinning band column. The product fraction, which boils at 66° at 4 mm pressure and melts at 53° – 5°, amounts to 13.6 parts and is identified by IR, NMR and microanalysis as bis (hexafluoroisopropyl) fumarate.

Analysis for $C_{10}H_4F_{12}O_4$: Calculated: C, 28.86; H, 0.97. Found: C, 28.59; H, 0.96.

EXAMPLE 6

Bis (1,1,2,2-Tetrahydroperfluorononylthiolo) Fumarate a. 1,1,2,2-Tetrahydroperfluorononyl mercaptan A mixture of 30.0 parts of 1,1,2,2-tetrahydroperfluorononyl iodide, 5.2 parts of thiourea and 150 parts by volume of ethanol is refluxed for 6 hours after which 12 parts of 25% sodium hydroxide solution is added dropwise with stirring and the resulting mixture refluxed for 1 hour. After cooling to room temperature, the reaction mixture is acidified with dilute sulfuric acid, 150 parts of water is added and the yellow organic layer is separated and dried over anhydrous magnesium sulfate. The product is then distilled through a short Vigreux column. In this manner, 13.7 parts of product boiling at 72° – 4° at 17 mm pressure is obtained. The product is identified as 1,1,2,2-tetrahydroperfluorononyl mercaptan by IR, NMR and microanalysis.

Analysis for $C_9H_5F_{15}S$: Calculated: C, 25.13; H, 1.17. Found: C, 24.68; H, 1.29.

b. Bis (1,1,2,2-Tetrahydroperfluorononylthiolo) Fumarate

A mixture of 3.7 parts of 1,1,2,2-tetrahydroperfluorononyl mercaptan and 0.65 parts of fumaryl chloride is placed in a 10 ml. flask and heated at 80° for 18 hours while passing a slow stream of nitrogen through the reaction flask. The resulting solid is dissolved in 7.0 parts by volume of α,α,α-trifluorotoluene and heated at 80° for an additional three hours. An additional 10 parts by volume of trifluorotoluene is added, the hot solution filtered, and the product allowed to crystallize slowly. After cooling, filtering, washing with cold trifluorotoluene, and drying, 0.85 parts of bis (1,1,2,2-tetrahydroperfluorononylthiolo) fumarate melting at 137.5° – 139° is obtained.

Analysis for $C_{22}H_{10}F_{30}S_2O_2$: Calculated: C, 28.03; H, 1.07. Found: C, 27.98; H, 1.12.

EXAMPLE 7

Bis (1,1,2,2-Tetrahydroperfluorohexyl) Fumarate

A mixture of 5.05 parts of fumaryl chloride and 17.0 parts of 1,1,2,2-tetrahydroperfluorohexanol, prepared as described in U.S. Pat. No. 3,283,012, is heated with stirring at 80° – 90° C under a nitrogen atmosphere until the liberation of hydrogen chloride ceases and VPC indicates that the starting materials are no longer present. The crude reaction mixture is recrystallized from hot hexane yielding 12.3 parts of a colorless semi-solid. Further purification is carried out by dissolving in 1,1,2-trichloro-trifluoroethane, passing through a neutral aluminum oxide column and evaporating the solvent. The product is still a semi-solid at room temperature, but IR, NMR and VPC indicate that it is pure.

Analysis for $C_{16}H_{10}F_{18}O_4$: Calculated: C, 31.60; H, 1.66; F, 56.24. Found: C, 31.57; H, 1.65; F, 56.02.

EXAMPLE 8

Bis (1.1 -Dihydroperfluorooctyl) Itaconate

A mixture of 12.52 parts of itaconyl chloride and 72.52 parts of 1.1-dihydroperfluorooctyl alcohol and 50 parts of benzotrifluoride is refluxed for 72 hours. The benzotrifluoride is then removed on a rotary evaporator and the residue is distilled twice under high vacuum. 34.6 Parts (yield 47.4%) of pure bis (1.1-dihydroperfluorooctyl) itaconate, boiling point 128° – 131° C at 0.1 mm Hg. pressure is obtained. Identification is made by microanalysis, IR and NMR.

Analysis for $C_{21}H_8O_4F_{30}$: Calculated: C, 28.20; H, 0.90; F, 63.74. Found: C, 24.41; H, 1.18; F, 64.00.

EXAMPLE 9

Bis (1.1-Dihydroperfluorooctyl) Malonate

A mixture of 14.8 parts of malonyl chloride, 84.02 parts of 1.1-dihydroperfluorooctyl alcohol and 200 parts of dry toluene was refluxed for 46 hours. The toluene was removed in a rotary evaporator and the residue was distilled under high vacuum. 37.54 parts (yield 86.5%) of pure bis (1.1-dihydroperfluorooctyl) malonate, boiling point 122° – 125° at 0.2 mm Hg. pressure is obtained. It is soluble at room temperature and melts at 35.5° – 36.5° C. Purity test and identification is made by VPC, IR and NMR.

Analysis for $C_{19}H_6F_{30}O_4$: Calculated: C, 26.28; H, 0.70; F, 65.65. Found: C, 26.14; H, 0.78; F, 65.32.

EXAMPLE 10

Bis (1-Methyl-1,2,2-Trihydroperfluorononyl) Fumarate a. 1-Methyl-1,2,2-Trihydroperfluorononyl nitrate To a solution of 18.7 parts of silver nitrate in 60 parts of acetonitrile is added dropwise with stirring 53.8 parts of 1-methyl-1,2,2-trihydroperfluorononyl iodide. The addition takes 50 minutes and there is no visible exotherm, but after a short time, a yellow solid begins to separate. Stirring is continued at room temperature for 72 hours, after which time the solid is removed by filtration. Water (100 parts) is added to the filtrate, the lower layer separated, dried over anhydrous magnesium sulfate, and distilled through an 18 inch spinning band column. In this manner, 32.5 parts of the desired 1-methyl-1,2,2-trihydroperfluorononyl nitrate, boiling at 77° – 79° at 4 mm pressure is obtained.

Analysis for $C_{10}H_6F_{15}NO_3$: Calculated: C, 25.38; H, 1.28; N, 3.03; F, 60.23. Found C, 25.19; H, 1.32; N, 3.34; F, 60.07.

b. 1-Methyl-1,2,2-Trihydroperfluorononyl alcohol

To a slurry of 44.7 parts of 60% sodium sulfhydrate in 100 parts by volume of ethanol is added dropwise in 1 hour 28.4 g of 1-methyl-1,2,2-trihydroperfluorononyl nitrate. The reaction is exothermic to 35° C. After stirring at room temperature for 1 hour, 250 parts of water is added, the bottom layer separated, washed again with water, and dried over anhydrous magnesium sulfate. Distillation through a short Vigreux column gives 20.5 parts of 1-methyl-1,2,2-trihydroperfluorononyl alcohol, boiling at 82° C at 100 mm. pressure.

Analysis for $C_{10}H_7F_{15}O$: Calculated: C, 28.05; H, 1.69; F, 66.56. Found: C, 28.15; H, 1.52; F, 66.35.

c. Bis (1-Methyl-1,2,2-Trihydroperfluorononyl) Fumarate

A mixture of 15.0 parts of 1-methyl-1,2,2-trihydroperfluorononyl, 2.68 parts of fumaryl chloride and 15.0 parts of triglyme is heated with stirring at 95° – 100° C for 32 hours and at 125° C for 35 hours until the evolution of hydrogen chloride ceases. After cooling to room temperature, water is added and the product extracted into ether. The ether solution is washed with 10% sodium bicarbonate, water and then dried over anhydrous magnesium sulfate. After evaporation of solvent, the product is distilled through a micro distillation apparatus. 6½ parts of the fraction boiling at 140° – 160° C at 0.050 mm pressure is obtained. This fraction analyzed only 68% product by VPC, so it was recrystallized two times from hot ethanol. In this manner, 3.0 parts of bis (1-methyl-1,2,2-trihydroperfluorononyl) fumarate, which is 99+% pure by VPC, is obtained.

Analysis for $C_{24}H_{14}F_{30}O_4$: Calculated: C, 30.78; H, 1.51; F, 60.87. Found: C, 30.44; H, 1.81; F, 60.92.

EXAMPLE 11

Using procedures of the foregoing examples employing stoichiometrically equivalent amounts of corresponding starting materials, the following compounds of FORMULA I are obtained.

FORMULA I

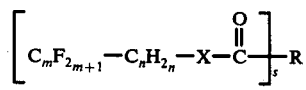

| | $C_mF_{2m+1}$ | $C_nH_{2n}$ | X | S | R |
|---|---|---|---|---|---|
| 11a | $(CF_3)_2CF$ | $CH_2CH_2$ | O | 2 | from citraconic acid |
| 11b | $CF_3(CF_2)_6$ | $(CH_2)_{10}$ | O | 2 | from fumaric acid |
| 11c | $CF_3(CF_2)_6$ | $CH_2$ | S | 3 | from aconitic acid |
| 11d | $CF_3(CF_2)_{17}$ | $CH_2CH_2$ | O | 2 | from fumaric acid |
| 11e | $(CF_3)_2(CF_2)_4$ | $(CH_2)_4$ | S | 2 | from mesaconic acid |
| 11f | $CF_3(CF_2)_8$ | $CH_2$ | O | 2 | from maleic acid |

EXAMPLE 12

10 Parts of bis (1,1-dihydroperfluorooctyl) fumarate and 0.2 parts of azodicyclo hexanecarbonitrile are sealed under nitrogen in an ampul and polymerized for 24 hours at 80° C. The resulting polymer is then dissolved in 90 parts of hexafluoroxylene and precipitated into 2000 parts of methanol.

The precipitated polymer is dried and identified by C, H and F analysis, and differential thermal analysis. The resulting polymer is dissolved in benzotrifluoride and applied to cotton and wool fabrics to obtain 2% of the polymer on the fabric. The oil and water repellency ratings are evaluated by a 3-M-Oil Test and the AATCC Water Spray Test referred to above, respectively.

In the following TABLE I, the analytical data for the polymer and its appearance is indicated together with the results of the repellency tests.

EXAMPLES 13 – 16

Following analogous procedures to those of EXAMPLE 12, homopolymers of the monomers indicated for the corresponding examples in the following table were obtained. Each such polymer was likewise tested for oil and water repellency and the results shown in TABLE I.

EXAMPLE 17

Equimolar amounts of bis (1.1-dihydroperfluorooctyl) malonate and formaldehyde (36% solution in water) are dissolved in four times their volume of acetone. To the resulting mixture 1% by weight of pyridine is added. After standing for four days at room temperature, two layers form. The bottom layer is separated, washed twice, and dried under vacuo. The dried material is a soft, white wax which is obtained in 54.5% yield. As in the previous EXAMPLES 12 through 16, the resulting polymers are dissolved in benzotrifluoride and applied to cotton and wool fabrics to obtain 2% of the polymer on the fabric and the repellency ratings determined. The results of analysis and repellency tests are indicated in TABLE I.

TABLE I

| Homopolymer of the Monomer: | Repellency 3-M-Oil | Repellency AATCC-Water | Appearance/ Yield % by Weight | $T_g$ (° C) | $T_m$ (° C) | Analysis Calc. | Analysis Found |
|---|---|---|---|---|---|---|---|
| 12 CH—COOCH$_2$C$_7$F$_{15}$ ‖ CH—COOCH$_2$C$_7$F$_{15}$ | C 120 W 140 | 70 70 | Sl. orange high viscous polymer 61.8% yield | −15 | +21 | C 27.29 H 0.69 F 64.75 | 27.54 0.88 63.92 |
| 13 CH—COO(CH$_2$)$_2$C$_7$F$_{15}$ ‖ CH—COO(CH$_2$)$_2$C$_7$F$_{15}$ | C 130 W 120 | 70 70 | Colorless, soft polymer 80.0% yield | +22 | +49 | C 29.09 H 1.11 F 62.75 | 29.33 1.45 61.67 |
| 14 CH—COO(CH$_2$)$_2$C$_4$F$_9$ ‖ CH—COO(CH$_2$)$_2$C$_4$F$_9$ | C 90 W 110 | | Colorless, soft polymer 19.6% yield | | | | |
| 15 CH—COOCH$_2$C$_3$F$_7$ ‖ CH—COOCH$_2$C$_3$F$_7$ | C 80 W 110 | 80 | Colorless, soft polymer 16.7% yield | +3 – 8 | +39 | C 30.01 H 1.26 F 55.40 | 29.39 1.89 55.20 |
| 16 CH$_2$=C—COOCH$_2$C$_7$F$_{15}$ ‖ CH$_2$—COOCH$_2$C$_7$F$_{15}$ | C 110 W 110 | 80 80 | Sl. yellow, high viscous polymer 52.5% yield | | | C 28.20 H 0.90 F 63.74 | 27.97 1.11 63.19 |

TABLE I-continued

| Homopolymer of the Monomer: | Repellency 3-M-Oil | AATCC-Water | Appearance/ Yield % by Weight | $T_g$ (° C) | $T_m$ (° C) | Analysis Calc. | Found |
|---|---|---|---|---|---|---|---|
| 17  $CH_2=C(COOCH_2C_7F_{15})_2$ | C  90<br>W  100 | 70 | White, waxy polymer<br>54.5% yield | | | C  27.29<br>H  0.69<br>F  64.75 | 26.13<br>1.09<br>64.62 |

EXAMPLE 18

10 Parts of a mixture of equimolar amounts of bis (1,1-dihydroperfluorooctyl) fumarate and the comonomers shown in the following TABLE II, 0.2 parts of azodicyclo hexanecarbonitrile and 20 parts of hexafluoroxylene are sealed under nitrogen in an ampul. Polymerization is carried out for 16 hours at 80° C and the resulting polymer solution diluted with 70 parts of hexafluoroxylene and precipitated dropwise with vigorous stirring into 200 parts of methanol. The precipitated polymer is dried and characterized by C and H analysis and differential thermal analysis. In each instance, the resulting copolymer is applied from a solution of benzotrifluoride so as to obtain 2% of the polymer on the fabric. In the following TABLE II, where two repellency values are indicated, the second indicates the values obtained when the copolymers obtained were blended with 60% by weight of poly-n-octyl methacrylate and the resulting blend applied to the fabrics in an amount of 2% by weight of the fabric. In each instance, the copolymer forms a 1:1 alternating copolymer.

TABLE II

| Comonomer | Repellency 3-M-Oil | AATCC-Water | Appearance | $T_g$ (° C) | $T_m$ (° C) | Analysis Calc. | Found |
|---|---|---|---|---|---|---|---|
| 18  $CH_2=CH-O-CH_3$ | C  120 (140)<br>W  140 (145) | 70 (70)*<br>70 (70) | White, brittle powder | +38 | +61 | C: 29.44<br>H: 1.29 | 29.12<br>1.34 |
| 19  $CH_2=CH-O-CH_2CH_3$ | C  120<br>W  120 | 80<br>80 | Sl. yellow rubbery | +27 | +52 | C: 30.78<br>H: 1.51 | 30.49<br>1.39 |
| 20  $CH_2=CH-O(CH_2)_3CH_3$ | C  110<br>W  110 | 70<br>— | White, tacky polymer | −5 | +40 | C: 31.85<br>H: 1.85 | 31.09<br>1.72 |
| 21  $CH_2=CH-O(CH_2)_9CH_3$ | C  80<br>W  70 | 70<br>— | Very viscous tacky polymer | −17 | +18 | C: 36.10<br>H: 2.84 | 34.37<br>2.31 |
| 22  $CH_2=CH-O(CH_2)_{11}CH_3$ | C  70<br>W  60 | 70<br>— | Viscous, tacky polymer | −18 | not distinct | C: 37.37<br>H: 3.14 | 35.95<br>2.86 |
| 23  $CH_2=CH-O(CH_2)_{15}CH_3$ | C  0<br>W  0 | 70<br>70 | Very tacky, high viscous oil | — | — | C: 39.73<br>H: 3.69 | 36.90<br>2.91 |
| 24  $CH_2=CH-O(CH_2)_{17}CH_3$ | C  0<br>W  0 | 70<br>70 | Very tacky, high viscous oil | — | — | C: 40.82<br>H: 3.94 | 37.92<br>3.20 |
| 25  $CH_2=CH-OCH(CH_3)_2$ | C  120<br>W  120 | 90<br>80 | White, sl. tacky polymer | +12 | +31 | C: 31.07<br>H: 1.67 | 30.35<br>1.43 |
| 26  $CH_2=CH-OCH_2CH(CH_3)_2$ | C  110<br>W  120 | 70<br>70 | Tacky polymer | +2 | +29 not dist. | C: 31.85<br>H: 1.85 | 31.48<br>1.48 |
| 27  $CH_2=CH-O(CH_2)_5CH(CH_3)_2$ | C  100<br>W  100 | 80<br>70 | Sl. yellow, tacky polymer | −30 | no sharp melt point | C: 34.76<br>H: 2.53 | 32.77<br>2.08 |
| 28  $CH_2=CH-OCH_2CH_2OCH_3$ | C  120 (130)<br>W  130 (140) | 70 (80)<br>70 (70) | Colorless, soft polymer | +8 − 14 | +48 | C: 30.56<br>H: 1.64 | 30.44<br>1.62 |
| 29  $CH_2=CH-OCH_2CH_2O(CH_2)_3CH_3$ | C  100<br>W  110 | 80<br>70 | Sl. yellow tacky | −30 − 36 | no sharp melt point | C: 32.83<br>H: 2.17 | 31.31<br>1.64 |
| 30  $CH_2=CH-OCH_2CF_3$ | C  110 (130)<br>W  140 (130) | 80 (80)<br>70 (70) | Colorless, soft polymer | +6 − 10 | not distinct | C: 28.64<br>H: 1.10 | 28.86<br>0.90 |
| 31  $CH_2=CH-OCH_2CH_2Cl$ | C  120 (120)<br>W  120 (130) | 80 (80)<br>80 (80) | White, brittle powder | +26 | +54 | C: 29.21<br>H: 1.33 | 29.18<br>1.60 |
| 32  $CH_2=CH-OCOCH_3$ | C  110 (130)<br>W  130 (140) | 70 (80)<br>80 (80) | White, brittle powder | −6 to −14 | +30 | C  29.83<br>H  1.25 | 29.99<br>1.27 |
| 33  $CH_2=CH-OCO(CH_2)_2CH_3$ | C  100<br>W  100 | 70<br>70 | Soft polymer | +13 | +32 | C  31.40<br>H  1.62 | 31.63<br>1.62 |
| 34  $CH_2=CH-OCO)CH_2)_4CH_3$ | C  100<br>W  110 | 70<br>70 | White, sl. tacky polymer | −15 | not dist. | C  32.89<br>H  1.97 | 31.57<br>1.59 |
| 35  $CH_2=CH-OCO)CH_2)_6CH_3$ | C  90<br>W  100 | 70<br>70 | Tacky, soft polymer | — | — | C  34.30<br>H  2.30 | 34.42<br>2.23 |
| 36  $CH_2=CH-OCO(CH_2)_{10}CH_3$ | C  90<br>W  80 | 70<br>— | Tacky polymer | −8 to +3 | +32 | C  36.90<br>H  2.92 | 36.88<br>3.02 |
| 37  $CH_2=CH-OCO-C_6H_5$ | C  80 (140)<br>W  120 (140) | 70 (70)<br>70 (70) | White, brittle polymer | not dist. | +48 | C  33.87<br>H  1.37 | 34.08<br>1.28 |
| 38  $CH_2=CH-OCOC(CH_3)_3$ | C  100<br>W  110 | 70<br>— | Soft polymer | +15 | +47 | C  32.16<br>H  1.80 | 32.10<br>1.96 |
| 39  $CH_2=C(CH_3)-OCOCH_3$ | C  130<br>W  130 | 70<br>70 | Very soft, rubbery polymer | — | — | C  30.68<br>H  1.52 | 30.08<br>1.52 |
| 40  $CH_2=C(CH_3)_2$ | C  110 (130)<br>W  140 (140) | 70 (80)<br>90 | White, fibrous brittle material | +12 | +58 | C  30.78<br>H  1.51 | 30.94<br>1.55 |
| 41  $CH_2=CH-CH_2CH_3$ | C  120<br>W  120 | 70<br>70 | Colorless soft polymer | not dist. | +59 | C  30.78<br>H  1.51 | 30.49<br>1.39 |
| 42  $CH_2=CH-(CH_2)_3CH_3$ | C  110<br>W  100 | 70<br>70 | Colorless soft polymer | −16 to −18 | not dist. | C  32.38<br>H  1.88 | 32.45<br>1.57 |
| 43  $CH_2=CH(CH_2)_5CH_3$ | C  110<br>W  90 | 70<br>70 | Colorless soft polymer | −28 to −39 | not dist. | C  33.88<br>H  2.33 | 31.76<br>1.68 |
| 44  $CH_2=CH-(CH_2)_7CH_3$ | C  100<br>W  100 | 70<br>70 | Colorless soft polymer | −30 to −35 | not dist. | C  35.31<br>H  2.57 | 32.20<br>1.74 |
| 45  $CH_2=CH-(CH_2)_9CH_3$ | C  100<br>W  90 | 70<br>70 | Colorless soft sl. tacky | ~−45 | not dist. | C  36.65<br>H  2.88 | 32.65<br>1.84 |
| 46  $CH_2=CH-(CH_2)_{11}CH_3$ | C  100<br>W  80 | 70<br>70 | Colorless soft sl. takcy | — | — | C  37.93<br>H  1.18 | 33.18<br>1.95 |
| 47  $CH_2=CH-(CH_2)_{15}CH_3$ | C  80<br>W  50 | 70<br>70 | Colorless, tacky polymer | — | — | C  40.29<br>H  3.79 | 34.20<br>2.09 |

TABLE II-continued

| | Comonomer | | Repellency 3-M-Oil | AATCC-Water | Appearance | $T_g$ (° C) | $T_m$ (° C) | | Analysis Calc. | Found |
|---|---|---|---|---|---|---|---|---|---|---|
| 48 | $CH_2=CH-\langle O \rangle$ | C W | 100 (110) 140 (140) | 70 (70) — | White, brittle polymer | +8 to +12° | ~+60 | C H | 34.16 1.43 | 35.20 1.77 |
| 49 | $CH_2=CH-\langle O \rangle-CH_3$ | C W | 100 140 | 70 — | White brittle polymer | no dist. | +38 | C H | 34.88 1.62 | 35.19 1.91 |
| 50 | $CH_2=CH-\langle O \rangle-Cl$ | C W | 100 100 | 70 — | White brittle polymer | not dist. | +37 | C H | 33.01 1.29 | 33.38 1.34 |
| 51 | $CH_2=CH-\langle O \rangle-OCH_3$ | C W | 100 100 | 70 — | White brittle polymer | +6 | +38 | C H | 34.33 1.59 | 34.82 1.59 |
| 52 | $CH_2=CH-N-CH_2\!\!\setminus_{CH_2}$ $\mid$ $CO-CH_2$ | C W | 110 130 | 70 — | White brittle powder | not dist. | +50 | C H | 31.50 1.53 | 30.98 1.48 |
| 53 | $CH_2=CH-N-CO\!\!\setminus_{CH_2}$ $\mid$ $CO-CH_2$ | C W | 110 130 | 70 — | White brittle powder | not dist. | +80 | C H | 31.06 1.31 | 31.95 1.61 |

*Values indicated in parenthesis in the Examples are those obtained employing a 40% blend of the polymer with 60% poly n-octyl methacrytate.

EXAMPLES 54-60

Following the general polymerization procedure of EXAMPLE 12 adjusting the amounts of reactants in accordance with the desired polymer end product, terpolymers of bis (1,1-dihydroperfluorooctyl) fumarate ($M_1$), di-n-octylfumarate ($M_2$), and methyl vinyl ether ($M_3$), having the constituent composition shown in TABLE III.

The repellency ratings were determined as described in EXAMPLE 12.

TABLE III

| Example | Copolymer Composition (% by wt.) $[(M_1)(M_3)]_n$ | $[(M_2)(M_3)]_m$ | Fluorinated Monomer (% by wt.) | | Repellency 3-M-Oil | AATCC-Water | Appearance | Analysis |
|---|---|---|---|---|---|---|---|---|
| 54 | 100 | | 93.8 | C W | 120(140) 140(145) | 70(70) 70(70) | White brittle powder | C: 29.12 H: 1.34 |
| 55 | 60.0 | 40.0 | 56.2 | C W | 140 140 | 70 — | White soft polymer | C: 45.41 H: 3.87 |
| 56 | 54.0 | 46.0 | 50.6 | C W | 130 130 | 70 80 | Soft sl. tacky polymer | C: 47.76 H: 5.26 |
| 57 | 48.5 | 51.5 | 45.5 | C W | 100 80 | 70 — | Tacky polymer | C: 49.98 H: 6.08 |
| 58 | 37.9 | 62.1 | 35.6 | C W | 90 50 | 70 — | Tacky viscous polymer | C: 54.23 H: 7.07 |
| 59 | 31.5 | 68.5 | 29.6 | C W | 70 0 | 70 — | Tacky viscous polymer | C: 56.78 H: 7.50 |
| 60 | 18.5 | 81.5 | 17.35 | C W | 0 0 | 70 — | Tacky viscous polymer | C: 91.98 H: 8.85 |

EXAMPLES 61-66

Following the polymerization procedure of EXAMPLE 12 adjusting the amounts of reactants in accordance with the desired block copolymer end product, block copolymers having the constituent composition indicated in TABLE IV were obtained.

The repellency ratings for each copolymer were determined as in the preceding examples.

TABLE IV

| Example | Composition (Mol %) Fluoro Monomer | Vinylacetate | Fluorinated Monomer Content (% b wt.) | F | Repellency (2% Polymer on Fabric) 3-M-Oil | ATTCC-Water |
|---|---|---|---|---|---|---|
| 61 | 50 | 50 | 91.2 | C W | 110 (130) 130 (140) | 70 (80) 70 (80) |
| 62 | 25 | 75 | 77.3 | C W | 110 140 | 70 — |
| 63 | 20 | 80 | 71.8 | C W | 120 140 | 80 — |
| 64 | 14.3 | 85.7 | 63.0 | C W | 110 140 | 70 — |
| 65 | 11.1 | 88.9 | 56.1 | C W | 110 140 | 70 — |
| 66 | 9.1 | 90.9 | 50.5 | C W | 110 140 | 70 — |

EXAMPLES 67-73

A 2% solution of the polymer of EXAMPLE 54 was blended with varying amounts of poly n-octylmethacrylate as indicated for EXAMPLES 67-73 tabulated in the following TABLE V. The repellency ratings of fabrics coated with 2% by weight of fabric of these polymer blends were determined as in the preceding example.

TABLE V

| Example | Composition of Blend | | Repellency | | |
|---|---|---|---|---|---|
| | Polymer of Ex. 54 % by wt. | P-Octylmethacrylate % by wt. | | 3-M-Oil | AATCC-Water |
| | 100 | 0 | C | 110 | 70 |
| | | | W | 145 | 70 |
| 67 | 40 | 60 | C | 140 | 70 |
| | | | W | 145 | 70 |
| 68 | 20 | 80 | C | 140 | 70 |
| | | | W | 145 | 70 |
| 69 | 10 | 90 | C | 140 | 80 |
| | | | W | 145 | 80 |
| 70 | 5 | 95 | C | 140 | 80 |
| | | | W | 140 | 80 |
| 71 | 4 | 96 | C | 140 | 70 |
| | | | W | 140 | — |
| 72 | 2 | 98 | C | 140 | 70 |
| | | | W | 140 | — |
| 73 | 1 | 99 | C | 100 | 70 |
| | | | W | 130 | — |

EXAMPLES 74–98

Alternating copolymers of the monomer bis (1,1,2,2-tetrahydroperfluorononyl) fumarate and the comonomers shown in TABLE VI for EXAMPLES 74–79 are made by following the polymerization procedure of EXAMPLE 12 employing the appropriate monomers. The analysis results for the polymers and repellency ratings for fabrics tested in the manner previously described are shown in the following TABLE VI.

In the same manner, alternating copolymers of the monomer bis (1,1-dihydroperfluorooctyl) itaconate and the comonomers shown in TABLE VI for EXAMPLES 80–87 are prepared following the procedure of EXAMPLE 22.

In EXAMPLE 88, an alternating copolymer of bis (1,1,2,2-tetrahydroperfluorooctyl) fumarate and methyl vinyl ether is made, analyzed and evaluated following the general methods of EXAMPLE 12, with the results shown in TABLE VI.

In EXAMPLES 89–92, following the methods of EXAMPLE 12 alternating copolymers of bis (1,1,2,2-tetrahydroperfluorohexyl) fumarate and the comonomers shown in TABLE VI are made, analyzed and evaluated.

In EXAMPLES 93 and 94, the monomer bis (1-methyl-1,2,2-trihydroperfluorononyl) fumarate forms alternating copolymers with the indicated comonomers following the procedure of EXAMPLE 12.

In a similar manner in EXAMPLES 95–98, the monomer bis (1,1,2,2-tetrahydroperfluorononylthiolo) fumarate is copolymerized to form alternating copolymers with comonomers indicated in TABLE VI following the procedure of EXAMPLE 12 except that the polymerizations were initially carried out at 100° C for 15 minutes to dissolve the monomer in hexafluoroxylene and then continued at 80° C for 16 hours.

TABLE VI

| | Comonomer | | Repellency | | Appearance | $T_g$ (° C) | $T_m$ (° C) | Analysis | |
|---|---|---|---|---|---|---|---|---|---|
| | | | 3-M-Oil | AATCC-Water | | | | Calc. | Found |
| 74 | $CH_2=CH-OCH_3$ | C | 120(120) | 70(70) | White, brittle polymer | +10 – 14 | +43 | C 29.31 | 30.90 |
| | | W | 130(140) | — | | | | H 1.71 | 1.78 |
| | | C/D | 110(120) | | | | | | |
| 75 | $CH_2=CH-OCO-CH_3$ | C | 120(110) | 70(80) | Sl. yellow brittle powder | +25 – 31 | +53 | C 31.40 | 31.00 |
| | | W | 140(120) | — | | | | H 1.62 | 1.55 |
| | | C/D | 130 | | | | | | |
| 76 | $CH_2=CH-OCO-\text{Ph}$ | C | 110(110) | 80(80) | White, brittle powder | +14– 18 | +60 | C 35.24 | 4.15 |
| | | W | 120(120) | — | | | | H 1.72 | 1.56 |
| 77 | $CH_2=CH-\text{Ph}$ | C | 100(110) | 70(70) | White, brittle powder | not distinct | +47 | C 35.59 | 36.07 |
| | | W | 110(110) | 70(70) | | | | H 1.79 | 1.87 |
| 78 | $CH_2=C(CH_3)_2$ | C | 120 | 70 | White, brittle powder | +26 | +51 | C 32.38 | 32.25 |
| | | W | 140 | 70 | | | | H 1.88 | 1.88 |
| 79 | $CH_2=CH-OCH_2CH_2OCH_3$ | C | 120(120) | 70(70) | White, sl. sticky polymer | not distinct | not dist. | C 32.09 | 31.01 |
| | | W | 130(120) | 70(70) | | | | H 2.00 | 1.70 |
| | | C/D | 120 | | | | | | |
| 80 | $CH_2=CH-OCH_3$ | C | 110 | 70 | Soft tacky polymer | +2 | not apparent | C 30.27 | 30.59 |
| | | W | 120 | 70 | | | | H 1.48 | 1.61 |
| 81 | $CH_2=CH-OCH_2CH_2OCH_3$ | C | 100 | 70 | Sl. yellow tacky polymer | –14 – 20 | not apparent | C — | — |
| | | W | 100 | — | | | | H — | — |
| 82 | $CH_2=CH-OCOCH_3$ | C | 110 | 70 | White, brittle polymer | not apparent | not apparent | C 30.63 | 31.05 |
| | | W | 120 | — | | | | H 1.44 | 1.44 |
| 83 | $CH_2=CH-OCO-\text{Ph}$ | C | 90 | 70 | White, brittle powder | +29 | 72 – 88 | C 34.56 | 33.69 |
| | | W | 100 | — | | | | H 1.60 | 1.60 |
| 84 | $CH_2=C(CH_3)_2$ | C | 100 | 70 | Soft, tacky polymer | — | — | C 31.59 | 30.98 |
| | | W | 80 | — | | | | H 1.70 | 1.58 |
| 85 | $CH_2=CH-\text{Ph}$ | C | 80 | 70 | White, brittle polymer | not dist. | not dist. | C 34.88 | 35.86 |
| | | W | 110 | — | | | | H 1.62 | 1.82 |
| 86 | $CH_2=CH-OCOC_7F_{15}$ | C | 110 | 70 | Tacky polymer | — | — | C — | — |
| | | W | 110 | — | | | | H — | — |
| 87 | $CH_2=C-Cl_2$ | C | 110 | 70 | Sl. yellow, brittle powder | +38 | +56 | C 27.85 | 28.52 |
| | | W | 100 | — | | | | H 1.02 | 1.25 |
| 88 | $CH_2=CH-OCH_3$ | C | 100(110) | 70(70) | soft polymer | +49 | +73 | C 31.88 | 33.00 |
| | | W | 110(130) | — | | | | H 1.86 | 2.31 |
| 89 | $CH_2=CH-OCH_3$ | C | 80 | 70 | Soft, sl. yellow | +4 to +7 | +35 | C 34.25 | 34.66 |

TABLE VI-continued

| | Comonomer | Repellency 3-M-Oil | AATCC-Water | Appearance | $T_g$ (° C) | $T_m$ (° C) | Analysis Calc. | Found |
|---|---|---|---|---|---|---|---|---|
| 90 | $CH_2=CH-OCOCH_3$ | W 90<br>C 80<br>W 90 | —<br>70<br>— | polymer<br>Soft, white<br>polymer | +5 | +35 | H 2.42<br>C 34.60<br>H 2.32 | 2.66<br>34.01<br>2.04 |
| 91 | $CH_2=CH-\bigcirc$ | C 70<br>W 80 | 70<br>— | Brittle, white<br>polymer | not dist. | not dist. | C 40.46<br>H 2.55 | 41.23<br>2.60 |
| 92 | $CH_2=CH-N\begin{array}{c}CO-CH_2\\ \\ CH_2-CH_2\end{array}$ | C 60<br>W 60 | 70<br>— | Brittle, white<br>polymer | +1 to +4 | +32 | C 36.73<br>H 2.66 | 36.28<br>2.68 |
| 93 | $CH_2=CH-OCH_3$ | C 100<br>W 100 | 70<br>— | White, brittle<br>polymer | — | — | C 32.61<br>H 2.03 | 33.06<br>2.16 |
| 94 | $CH_2=CH-OCOCH_3$ | C 100<br>W 100 | 70<br>— | White, brittle<br>polymer | — | — | C 32.89<br>H 1.97 | 32.61<br>2.10 |
| 95 | $CH_2=CH-OCH_3$ | C 120<br>W 140 | 100<br>100 | White, brittle<br>polymer | not dist. | +118° | C 30.07<br>H 1.62 | 30.63<br>1.74 |
| 96 | $CH_2=CH-OCOCH_3$ | C 130(130)<br>W 140(140) | 80(100)<br>— | White, brittle<br>polymer | not dist. | +103° | C 30.42<br>H 1.57 | 29.90<br>1.97 |
| 97 | $CH_2=C(CH_3)_2$ | C 120<br>W 120 | 50<br>— | White, brittle<br>polymer | not dist. | +48° | C 31.34<br>H 1.82 | 32.25<br>2.23 |
| 98 | $CH_2=CH-\bigcirc$ | C 110<br>W 140 | 80<br>— | White, brittle<br>polymer | not dist. | +75° | C 34.49<br>H 1.74 | 34.45<br>2.04 |

EXAMPLES 99–107

In EXAMPLES 99–107 the general polymerization procedure of EXAMPLE 12 is employed except that benzotrifluoride is used as the solvent instead of hexafluoroxylene.

Bis (1,1-dihydroperfluorobutyl) fumarate monomer and the comonomers shown in EXAMPLES 99–103 of TABLE VII form alternating copolymers.

Bis (hexafluoroisopropyl) fumarate monomer is copolymerized with the comonomers shown in TABLE VII for EXAMPLES 104–107 to form alternating copolymers.

TABLE VII

| | Comonomer | Repellency 3-M-Oil | AATCC-Water | Appearance | $T_g$ (° C) | $T_m$ (° C) | Analysis Calc. | Found |
|---|---|---|---|---|---|---|---|---|
| 99 | $CH_2=CH-OCH_3$ | C 80<br>W 100 | 70<br>70 | White, slightly<br>tacky polymer | +22 – 25 | not dist. | C 33.47<br>H 2.25 | 33.65<br>2.39 |
| 100 | $CH_2=CH-OCH_2CF_3$ | C 80<br>W 80 | 80<br>70 | White powdery<br>polymer | +20 – 30 | +54 | C 31.70<br>H 1.83 | 31.57<br>1.83 |
| 101 | $CH_2=CH-OCH_2CH_2Cl$ | C 70<br>W 70 | 70<br>70 | White powdery<br>polymer | — | — | C —<br>H — | —<br>— |
| 102 | $CH_2=CH-OCOCH_3$ | C 90<br>W 100 | 70<br>70 | White, brittle<br>polymer | not dist. | +51 | C 33.94<br>H 2.14 | 34.98<br>2.45 |
| 103 | $CH_2=C(CH_3)_2$ | C 70<br>W 80 | 70<br>70 | White, brittle<br>polymer | — | — | C 35.83<br>H 2.63 | 36.06<br>2.57 |
| 104 | $CH_2=CH-OCH_3$ | C 70<br>W 80 | 70<br>70 | White, brittle<br>polymer | +58 – 61 | no melt | C: 32.92<br>H: 2.13 | 32.89<br>2.02 |
| 105 | $CH_2=CH-OCH_2CF_3$ | C 0<br>W 0 | 80<br>— | White, brittle<br>polymer | +48 – 59 | no melt peak | C: 31.01<br>H: 1.67 | 31.07<br>1.86 |
| 106 | $CH_2=CH-OCOCH_3$ | C 70<br>W 50 | 70<br>— | White, brittle<br>polymer | — | — | C: 33.48<br>H: 2.01 | 33.41<br>1.98 |
| 107 | $CH_2=C(CH_3)_2$ | C 60<br>W 60 | 70<br>— | White, brittle<br>polymer | not dist. | not dist.<br>+141 | C: 35.60<br>H: 2.56 | 35.66<br>2.72 |

EXAMPLE 108

A monomer mixture is compounds of FORMULA I prepared from a telomer mixture is copolymerized with methyl vinyl ether as a comonomer according to the procedure of EXAMPLE 12 to give alternating copolymers.

The monomer of FORMULA I is one in which $n$ is 2, X is oxygen, $s$ is 2, R is derived from fumaric acid and $C_mF_{2m+1}$ is comprised by weight of 34.2% of $C_6F_{13}$, 38.7% of $C_8F_{17}$, and 26.0% of $C_{10}F_{21}$.

The oil repellency of fabric treated with a solution of this copolymer is as follows. (2% by weight on the fabric.)

| 3-M-Oil Test: | Cotton | 110(120) |
|---|---|---|
| | Wool | 130(140) |
| | Cotton/Polyester | 110(130) |

EXAMPLE 109

A monomer mixture of compounds of FORMULA I as defined in EXAMPLE 108 is prepared from a telomer mixture. $C_mF_{2m+1}$ is comprised by weight of: 85.3% of $C_8F_{17}$ and 11.0% of $C_{10}F_{21}$.

The mixture of fluorinated monomer is copolymerized with methyl vinyl ether and the oil repellency of fabric having 2% by weight of the fabric of the resulting copolymer thereof is determined.

| 3-M-Oil Test: | Cotton | 120(140) |
|---|---|---|
| | Wool | 130(140) |
| | Cotton/Polyester | 120(40) |

The mixture of fluorinated monomer is also copolymerized with vinyl acetate. The repellency of fabric having 2% by weight of the fabric of the resulting copolymer thereon is determined.

| 3-M-Oil Test: | Cotton | 120(120) |
|---|---|---|

| -continued | |
|---|---|
| Wool | 130(140) |
| Cotton/Polyester | 130(130) |

While the invention has been explained by detailed description of certain specific embodiments, it is understood that various modifications and substitutions can be made in any of them within the scope of the appended claims which are intended also to include equivalents of such embodiments.

What is claimed is:

1. A compound of the formula:

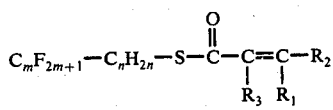

wherein
  $m$ is 6 to 12,
  $n$ is 1 or 2,
  $R_1$ and $R_2$ are (a) hydrogen, (b) methyl, or

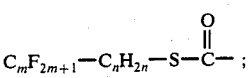

wherein $m$ and $n$ are as defined above; and $R_3$ is (a) hydrogen;

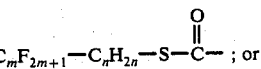

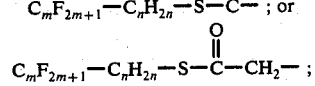

wherein $m$ and $n$ are as defined above;
provided that when
  $R_1$ is (a), $R_2$ is (a), and $R_3$ is (c) or (d); or
  $R_1$ is (a), $R_2$ is (c), and $R_3$ is (a) or (d); or
  $R_1$ is (b), $R_2$ is (c), and $R_3$ is (a); or
  $R_1$ is (c), $R_2$ is (a), and $R_3$ is (a) or (d); or
  $R_1$ is (c), $R_2$ is (b), and $R_3$ is (a).

2. Bis (1,1,2,2-tetrahydroperfluorononylthiolo) fumarate.

* * * * *